United States Patent
Quan (10) Patent No.: US 11,344,484 B2
(45) Date of Patent: *May 31, 2022

(54) PROCESS FOR MAKING TRANSPARENT NANOEMULSIONS COMPRISING LAURIC OIL

(71) Applicant: Conopco, Inc., Trumbull, CT (US)

(72) Inventor: Congling Quan, Woodbridge, CT (US)

(73) Assignee: CONOPCO, INC., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/961,945

(22) PCT Filed: Jan. 21, 2019

(86) PCT No.: PCT/EP2019/051344
§ 371 (c)(1),
(2) Date: Jul. 14, 2020

(87) PCT Pub. No.: WO2019/145248
PCT Pub. Date: Aug. 1, 2019

(65) Prior Publication Data
US 2020/0345598 A1 Nov. 5, 2020

(30) Foreign Application Priority Data

Jan. 23, 2018 (EP) .................................... 18152922

(51) Int. Cl.
*A61K 8/06* (2006.01)
*A61K 8/36* (2006.01)
*A61K 8/37* (2006.01)
*A61Q 19/00* (2006.01)
*A61Q 19/10* (2006.01)

(52) U.S. Cl.
CPC .............. *A61K 8/068* (2013.01); *A61K 8/361* (2013.01); *A61K 8/37* (2013.01); *A61Q 19/007* (2013.01); *A61Q 19/10* (2013.01)

(58) Field of Classification Search
CPC ........ A61K 8/345; A61K 8/361; A61K 8/375; A61K 8/062; A61K 2800/21; A61Q 19/10
See application file for complete search history.

(56) References Cited

U.S. PATENT DOCUMENTS

| | | | |
|---|---|---|---|
| 6,544,530 B1 * | 4/2003 | Friedman | A61K 8/06 424/400 |
| 7,393,548 B2 | 7/2008 | Friedman | |
| 8,834,903 B2 | 9/2014 | Simonnet et al. | |
| 9,149,418 B2 | 10/2015 | Desenne et al. | |
| 2006/0036222 A1 | 2/2006 | Cohen et al. | |
| 2017/0112764 A1 | 4/2017 | Wu | |

FOREIGN PATENT DOCUMENTS

| | | |
|---|---|---|
| EP | 2343036 | 12/2010 |
| WO | WO2017182262 | 10/2017 |
| WO | WO2017182264 | 10/2017 |

OTHER PUBLICATIONS

Search Report and Written Opinion in EP18152915; dated Jun. 20, 2018.
Search Report and Written Opinion in EP18152922; dated Aug. 18, 2016.
Search Report and Written Opinion in PCTEP2019051342; dated Mar. 22, 2019.
Search Report and Written Opinion in PCTEP2019051344; dated Mar. 22, 2019.
Co-pending Application, Congling Quan, Jul. 14, 2020, U.S. Appl. No. 16/961,943.

* cited by examiner

*Primary Examiner* — Michael P Cohen
(74) *Attorney, Agent, or Firm* — Krista A. Kostiew

(57) ABSTRACT

The invention relates to oil-in-water emulsion in which specific oils (e.g., lauric oils) are used in the oil phase while surprisingly maintaining excellent transparency. In one aspect, said emulsions comprise fatty acid in oil phase. The invention comprises an energy efficient process for making said fatty acid containing transparent nanoemulsions.

18 Claims, 1 Drawing Sheet

Fig. 1

Not using concentrate-dilution

Fig. 2

Concentrate-dilution process

PROCESS FOR MAKING TRANSPARENT NANOEMULSIONS COMPRISING LAURIC OIL

CROSS REFERENCE TO RELATED APPLICATIONS

The present application is a U.S. National Phase Application under 35 U.S.C. § 371 of International Application No. PCT/EP2019/051344, filed on Jan. 21, 2019, which claims priority to European Patent Application No. 18152922.3, filed on Jan. 23, 2018, the contents of which are incorporated herein in their entireties.

FIELD OF THE INVENTION

The present invention relates to novel oil-in-water nanoemulsions and process for making. The internal phase comprises lauric oils, such as coconut oil, palm kernel oil and mixtures thereof. Highly saturated oils such as these are used for skin moisturization, but are not considered suitable for use in oil continuous transparent cleansing compositions because such oils are typically opaque and semi-solid (due to high degree of saturation) at ambient temperature. Surprisingly, when lauric oils are used, excellent transparency is achieved, particularly in systems comprising anionic cleansing surfactant in the aqueous phase and high levels of glycerol. Further, nanoemulsions, preferably having at least minimal levels of amphoteric surfactant in the aqueous phase, permits good foaming. The specific process of the claimed invention is a concentrate-dilution process where fatty acid(s) is in internal oil phase and wherein the process provides remarkable transparency (<45 NTU) very efficiently (one pass through high pressure homogenizer only).

BACKGROUND OF THE INVENTION

Generally, oil continuous transparent cleansing oil compositions, such as Dove® Nourishing Care shower oil, are desirable because such compositions are attractive (consumers desire transparent compositions) while simultaneously providing excellent cleansing and moisturization (e.g., the oils are moisturizing agents).

Such transparent oil compositions are typically delivered in the form of oil soluble surfactants which are solubilized in liquid vegetable oils, such as sunflower oil, soybean oil etc. These vegetable oils are typically high in oleic (18:1), and linoleic (18:2) acid. The high level of unsaturation makes this composition prone to oxidation. Oil soluble surfactants used in these systems typically also provide much poorer lather performance (lather being another desirable attribute) than typical anionic and amphoteric cleansing surfactants.

Coconut and palm kernel oil contain high levels of medium- and long-chain saturated fatty acids. Both oils are rich in lauric acid. For purposes of our invention, oils that contain high level of lauric acid (12:0), saturated $C_{12}$ length fatty acid (30% or more of fatty acid composition of the oil or oils), are called lauric oils. The high level of saturation makes lauric oils stable against oxidation; however, such highly saturated oils have higher melting point compared with other liquid vegetable oils. Because they become semi-solid (due to high melting point) at ambient temperature, they would not be considered suitable for use in oil continuous cleansing liquid compositions which are transparent.

There is thus a need to develop a cleansing composition that is rich in lauric oils (will not oxidize as readily as more unsaturated oils) which can retain excellent transparency and which can further provide satisfactory lather.

Transparent nanoemulsions are known in the prior art. U.S. Pat. No. 8,834,903 to Simonnet et al. discloses nanoemulsions which are said to be transparent comprising an oil phase which may contain oils chosen from oils of animal or vegetable origin (column 4, lines 25-26), and further comprising non-ionic surfactant, sugar fatty esters or sugar fatty ethers, with transparency measured by Nephelometric Turbidity Unit, or NTU, values ranging 60 to 600 NTU. It further discloses the emulsions comprise glycols, such as glycerol to help improve the transparency of the formulation.

U.S. Pat. No. 7,393,548 to Friedman discloses cosmetic or pharmaceutical compositions in the form of oil-in-glycerin emulsion to facilitate stratum-corneum penetration and dermal penetration of bioactive compound. The oil may be coconut oil although there is no recognition of advantage of one type of oil versus another regarding transparency. The reference makes no mention of transparency. There is also no disclosure of surfactant systems comprising anionic surfactant.

Nanoemulsion compositions comprising triglyceride oils in an internal phase and anionic surfactant(s) in an external aqueous phase are also not new. Applicants have filed applications (e.g., EP Application No. 16166487) directed to (1) an internal phase comprising triglycerides oils and/or petrolatum (as well as fatty acid); and (2) an external phase having specific surfactant (e.g., amino acids based surfactants). There is no disclosure in this application of such compositions being transparent or that such transparency is achievable in the presence of specific types of oils. There is no disclosure that, if using fatty acids, the melting point of fatty acid or of a mixture of fatty acids is further critical to achieving transparency. There is no recognition of processing criticalities and no disclosure of formation of transparent nanoemulsion comprising fatty acid, especially an energy efficient process for making particularly high transparency compositions, such as disclosed by applicant in the subject application.

None of the references above describes nanoemulsions comprising highly saturated lauric oils (i.e., that will not readily oxidize) which maintain excellent transparency; and which simultaneously provide satisfactory lather as well as desirable moisturization. Further, none of the references disclose a method for preparing the transparent lauric oil nanoemulsions in an efficient way such as disclosed in the subject invention.

SUMMARY OF THE INVENTION

In a co-pending application, applicants disclose lauric oil nanoemulsions that maintain excellent transparency and which comprise highly water soluble anionic and/or amphoteric cleansing surfactants. The compositions are efficiently prepared with at least one pass through a homogenizer at a pressure of 7,000 psi or less (482.6 bar or less; to convert from psi to bar, we divide the pressure value by 14.504), and the resulting composition simultaneously provides desirable moisturization (from oils and humectants present), satisfactory lather, and highly transparent compositions (measured by Nephelometric Turbidity Unit, or NTU, values less than 100, preferably less than 60) desirable to the consumer. The subject application is directed to specific concentrate-dilution process where only one pass through homogenizer is needed (more energy efficient) while providing final compositions having less than 45 NTU.

More specifically, in one aspect, subject of a co-pending application, compositions of the invention comprise an oil-in-water nanoemulsion wherein said nanoemulsion comprises:

1) an internal oil phase comprising 3.5% to 40%, preferably 5 to 40% or 10% to 40% by wt. nanoemulsion composition of a lauric oil, said lauric oil defined as an oil(s) wherein saturated $C_{12}$ length fatty acid (12:0) comprises 30% or more, preferably 30 to 85% of the fatty acid composition of the oil or oils. Preferably, the oil is an oil selected from the group consisting of coconut oil, palm kernel oil, various other lauric oils noted below and mixtures thereof; and
2) an external aqueous phase comprising:
   i. 55 to 90% by wt. nanoemulsion of water and glycerol, wherein the ratio of said glycerol to said water is 2.5:1 and higher, preferably 2.8:1 to 10:1 or 3:1 to 5:1; and
   ii. 3 to 12% of a surfactant system comprising water soluble surfactants selected from the group consisting of anionic surfactants, amphoteric surfactants and mixtures thereof, wherein said anionic surfactant comprises 15% or more, preferably 40% or more (up to 100%, preferably 95%, although preferably it is 40% to 85%, or 50% to 85%, that is, there is at least some amphoteric surfactant) of the total surfactant system;
   wherein said composition has a Turbidity of less than 100 NTU, preferably less than 90 NTU, more preferably 80 to 1 NTU or 70 to 2 NTU, most preferably 60 to 5 NTU.

The nanoemulsion of the co-pending invention is typically prepared by combining an oil phase comprising lauric oil(s) and an aqueous phase comprising surfactant, glycerol and water in a conventional mixer, and passing the mixture through a homogenizer for 1 or 2 passes (or more if desired) at homogenization pressure of 7000 psi (pounds per square inch) or less (482.6 or less bar), preferably 1500 psi to 5500 psi (103.4 to 379.2 bar). The greater the number of passes, the lower the NTU value (see Example 7 versus Example 8). Alternatively, the nanoemulsion can be prepared by simultaneously pumping the oil phase and aqueous phase into a homogenizer, without being mixed in a conventional mixer.

The temperature for preparing the nanoemulsion is from ambient temperature to 60° C.

Preferably, the volume average diameter, D[4,3], of oil droplets is 100 nm or lower, more preferably 20 to 95 or 30 to 85 or 40 to 75.

Unexpectedly, nanoemulsion delivering excellent moisturizing oils, humectant (e.g., glycerol) and good foaming attributes, all while maintaining excellent transparency, can be obtained.

In another aspect, compositions of which are made using concentrate-dilution process of the subject invention, the internal oil phase further comprises (requires) 0.1 to 7% by wt. nanoemulsion composition of a fatty acid or fatty acid mixture, wherein the melting temperature of the fatty acid or mixture of fatty acids is −10° C. to 30° C., preferably 0° C. to 25° C., or 5° C. to 20° C. Fatty acids or mixture of fatty acids with a melting temperature higher than 30° C. tend to cause haziness and gelling in the nanoemulsion, resulting in non-transparent nanoemulsions at ambient temperature (Comparatives F and G). Of course, if heated, e.g., at above 40° C., the composition is both fluid and transparent. Fatty acid(s) may also be used in non-concentrate-dilution process, but they are not required.

In another aspect of the invention, the subject of the current application, the efficiency of making a transparent nanoemulsion comprising fatty acid can be further improved. Specifically, the invention relates to a concentrate-dilution process, a less energy intensive process (e.g., using one pass only through a high pressure homogenizer), to obtain nanoemulsion compositions having free fatty acid (s) in the oil phase and a turbidity of 45 NTU or less, preferably 40 NTU or less or 35 NTU or less or 30 NTU or less. The concentrate-dilution process comprises
   a) first preparing an intermediate concentrate emulsion containing:
      i. an oil phase additionally comprising fatty acid or mixture of fatty acids having melting point −10° C. to 30° C.; where said oil phase comprises 50 to 85% of the said concentrate emulsion and fatty acid or mixture comprises 1 to 15% of the said concentrate emulsion; and
      ii. an aqueous phase comprising a surfactant system, glycerol and water wherein the ratio of said glycerol to said water is 1:2 to 2:1, and said aqueous phase comprises 15 to 50% of the said concentrate emulsion;
      iii. heating aqueous and oil phase to a temperature ranging from ambient to 60° C. separately; and
      iv. a) mixing said aqueous phase and said oil phase in a conventional mixer equipped with a rotor/stator high shear device at rotor speed of 3000 to 7000 rpm to form concentrate emulsion; or
      b) alternatively pumping both aqueous and oil phase simultaneously through a low pressure homogenizer at pressure of 200 to 500 psi (13.8 to 34.5 bar) to form concentrate emulsion;
      wherein the said surfactant system comprises water soluble surfactants selected from the group consisting of anionic surfactants, amphoteric surfactants and mixtures thereof, wherein said anionic surfactant comprises 15% or more, preferably 40% or more (up to 100%, preferably 95%, although preferably it is 40% to 85%, or 50% to 85%, that is, there is at least some amphoteric surfactant) of the total surfactant system.
      wherein the said surfactant system comprises 3.5 to 12% of the said concentrate emulsion.
      wherein oil droplets formed in said concentrated emulsion have an average particle size, D[4,3], of 100 to 350 nm, preferably 110 to 250 nm.
   b) diluting the concentrate emulsion with glycerol and anionic and/or amphoteric cleansing surfactant solution to oil range of 3.5 to 40%, preferably 5 to 39 or 10 to 38% by wt. emulsion and to the ratio of glycerol to water ranging from 2.5:1 and higher, preferably 2.8:1 to 10:1 or 3:1 to 5:1; and
   c) passing the diluted emulsion through a high pressure homogenizer at pressure of 6000 psi or less (413.6 bar or less), preferably 1500 to 5000 psi (103.4 to 344.7 bar), wherein pass through high pressure homogenizer of step (c) is done only once and results in said final oil-in-water nanoemulsion having, subsequent to preparation of concentrate emulsion and dilution, a turbidity of less than 45 NTU.

This concentrate-dilution process is advantageous over the process typically used in the non-concentrate-dilution application because it allows use of only a single pass through high pressure homogenizer (much less energy intensive) while providing better transparency (Measured by turbidity of 45 NTU or less; 40 NTU or less, or 35 NTU or less) than the transparency reached in the non-concentrate-dilution process when only one pass through high pressure homogenizer is used (see Examples 7, used as a Comparative for this process, compared to Example 12c).

DETAILED DESCRIPTION OF THE INVENTION

Figure 1:
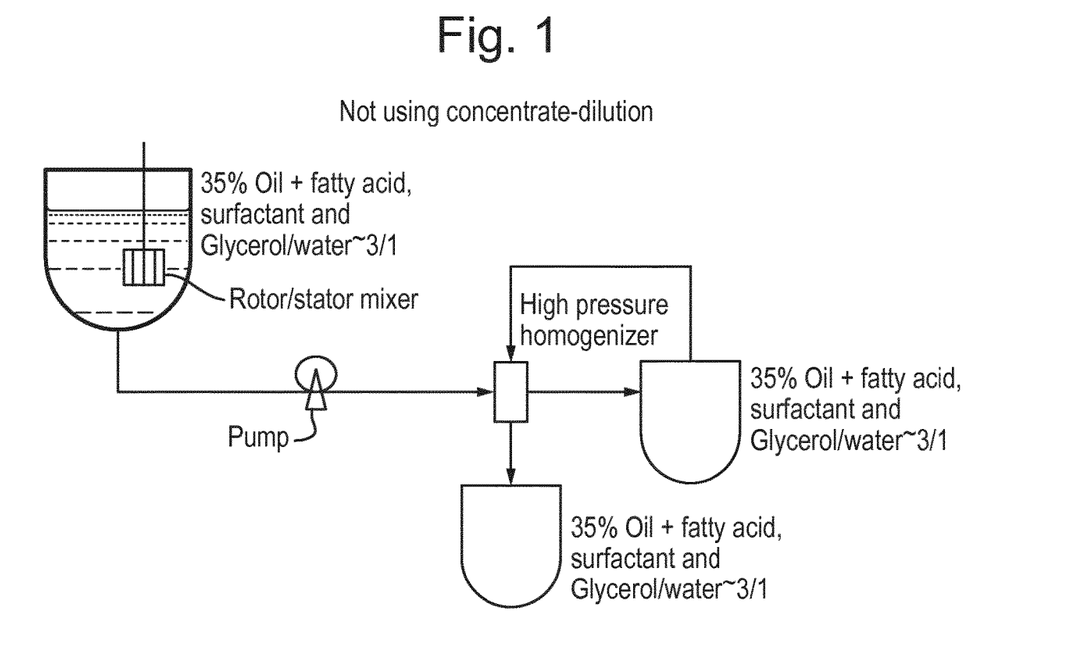
FIG. 1 is schematic of typical process which does not use concentrate, followed by dilution.
Figure 2:
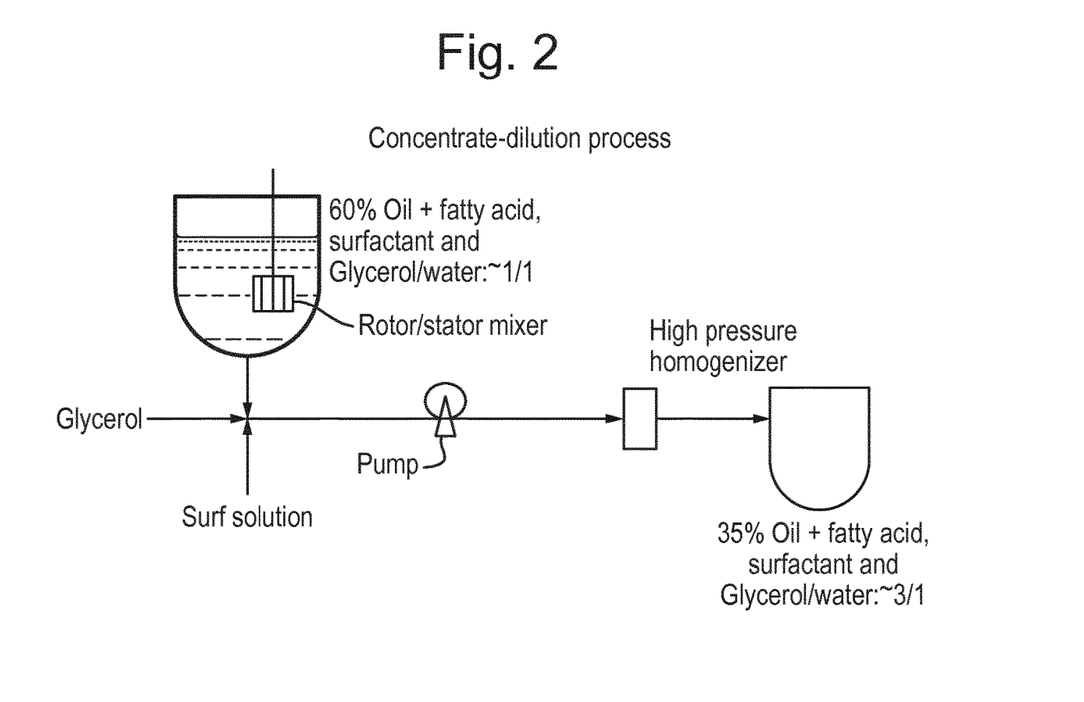
FIG. 2 is schematic of process where concentrate is formed, followed by dilution.

Except in the operating and comparative examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

It should be noted that in specifying any range of concentration or amount, any particular upper concentration can be associated with any particular lower concentration or amount.

For the avoidance of doubt the word "comprising" is intended to mean "including" but not necessarily "consisting of" or "composed of." In other words, the listed steps, options, or alternatives need not be exhaustive.

The disclosure of the invention as found herein is to be considered to cover all embodiments as found in the claims as being multiply dependent upon each other irrespective of the fact that claims may be found without multiple dependency or redundancy.

Nanoemulsions of the subject invention are able to deliver excellent moisturizing lauric oils, highly saturated oils which have high melting point and typically would be expected to result in opaque oil continuous cleansing compositions (because high melting point makes them seem solid and they're opaque). Unexpectedly, using these lauric oils as internal phase, using defined ratio of glycerol to water, mixing under relatively less energy intensive process (generally using at least 1 pass through homogenizer at 7000 psi or less, although the process of claimed invention uses one pass only through high pressure homogenizer), and using highly water soluble anionic and/or amphoteric surfactants in the aqueous phase of the nanoemulsions, it is possible to obtain compositions which retain excellent transparency and further provide good foam. The compositions further provide moisturization from oils (lauric oils) and humectant (e.g., glycerol).

In another aspect, the invention provides nanoemulsions additionally comprising fatty acid or fatty acid mixtures in the oil phase having defined melting temperature of such fatty acid or mixture (−10° C. to 30° C.). Fatty acid(s) is optional in non-concentrate-dilution process but required in the concentrate-dilution process. In the process claimed by the subject application, the invention provides even less energy intensive method (one pass through high pressure homogenizer) of making nanoemulsion comprising said oil phase which additionally comprises fatty acid or mixture of fatty acids while obtaining excellent transparency values obtainable in non-concentrate-dilution process only if at least two passes are used.

The invention is defined with more particularity below.

Oil Phase

Vegetable oils are frequently used in cosmetic compositions as moisturizers. The main constituent of vegetable oil is triglyceride or triacylglycerol, an ester derived from a glycerol and three fatty acids. The composition of the fatty acid ester-linked to the glycerol moiety respectively defines the physical and chemical properties of triglyceride oils. Frequently used vegetable oils in cosmetic compositions such as sunflower oil and soybean oil are liquid at ambient temperatures and prone to oxidation due to the high level of unsaturated components, e.g. oleic (18:1), and linoleic (18:2) acid, in their fatty acid composition. Hence their iodine value (a measure of the amount of unsaturation in the oils, expressed in the mass of iodine in grams that is consumed by 100 grams of oil) is typically in the range of 80 to 140.

Oils in the internal phase of the oil-in-water nanoemulsion (of both co-pending and the subject invention) are lauric oils, a group of oils that are high in lauric acid (12:0), present at levels between 30 and 85%, unlike most of vegetable oils. Lauric oils of our invention also typically contain 5 to 20% medium chain $C_8$ and $C_{10}$ saturated fatty acid. The lauric oils include coconut oil, palm kernel oil, babassu, tukum, murumuru, ouricuri, cohune, some *cuphea* oils and lauric algal oil. Coconut and palm kernel oil are most commercially developed while the others are to a lesser degree. Preferred oils in the internal phase of the subject invention are coconut oil, palm kernel oil and mixtures thereof. Typically, IV value of lauric oils of the invention is 50 or below, for example, 0.5 to 50.

Coconut oil is an edible oil derived from the coconut palm (*Cocus nucifera*). Palm-kernel oil is produced from the kernels of the oil palm. Both contain high levels of medium- and long-chain saturated fatty acids. Both oils are rich in lauric acid, but differ in their levels of caprylic (8:0), capric (10:0) and oleic (18:1) acids. Coconut oil is more saturated than palm kernel oil, hence the iodine value of the former is lower than the latter at 6-10 and 14-21 respectively. This is well below typical iodine values of above 50, typically 80 to 140 typically found in oils such as sunflower oil and soybean oil as noted above. Because highly saturated lauric oils of our invention are high in saturated content, they are slow to oxidize compared with other vegetable oils. Slow oxidation is an important component of our invention.

The fatty acid composition of typical lauric oils of our invention is noted in the Table below.

| Typical Fatty Acid Composition (% wt.) of Lauric Oils Adapted from Gunstone* | | | | | | | | |
|---|---|---|---|---|---|---|---|---|
| Oil source | 8:0 | 10:0 | 12:0 | 14:0 | 16:0 | 18:0 | 18:1 | 18:2 |
| Coconut | 8 | 7 | 48 | 16 | 9 | 2 | 7 | 2 |
| Palm kernel | 3 | 4 | 45 | 18 | 9 | 3 | 15 | 2 |

*F. D. Gunstone, in W. Hamm and R. J. Hamilton, eds., *Edible Oil Processing*, Sheffield Academic Press, Sheffield, U.K., 2000, pp. 1-33.

The melting point of coconut oil and palm kernel oil is 23 to about 26° C. and 23 to about 30° C. respectively.

Lauric oils can be hydrogenated (i.e., made even more saturated) to further enhance their stability and color. Hydrogenation increases the melting point of coconut and palm kernel oil to about 32° C. and about 40° C. respectively.

Although these lauric oils are excellent moisturizing oils, they would not be contemplated for use in oil continuous transparent cleansing compositions because these oils are typically semi-solid at ambient temperature, due to their high degree of saturation.

The lauric oils, when used in the subject application, typically range from 5 to 40% (assuming all the oils in the oil phase are lauric oils) by wt. of total nanoemulsion composition. The preferred volume average diameter of the droplet (measured as D[4,3]) is 100 nm or lower, preferably 20 to 95 or 30 to 85 or 40 to 75. Meanwhile, the intermediate concentrate emulsion of the subject application, comprises oil at greater than 45% to 85% and yields oil droplets of 100 to 350 nm (volume average diameter, measured as D[4,3]).

Surprisingly, applicants have found that, unlike the lauric oils of our invention, not all triglyceride based oils, will form transparent compositions, even when using the compositions and processes of the subject invention. For example, in one composition example, applicants show that sunflower oil (a high oleic oil with an iodine value of 87), used in a composition which is identical except that coconut oil is used, has a turbidity value of 163 NTU versus 32.8 NTU when the more saturated coconut oil is used (see Comparative A versus Example 1). It should be noted that some small amount of non-lauric triglyceride oils, which typically have a higher level of unsaturation (iodine value of above 50), for example sunflower oil, grape seed oil, argan oil etc. may be used as partial replacement for the 5-40% lauric oils in the oil phase of nanoemulsions. However, they should not replace more than 30% of such lauric oils in order to maintain the transparency and, there is minimum 5% oil (i.e., minimum 5% total lauric oil and non-lauric oil). Specifically, if there is 5% total oil as percent of nanoemulsion, in theory the oil phase may comprise 1.5% non-lauric oil (30% of 5%) and 3.5% lauric oil. So total lauric oil may be 3.5% to 40% lauric oil. Conversely, the 5 to 40% oil in the oil phase may be 100% lauric oils.

*Cuphea* oil is another lauric oil which may be used. It is pressed from the seeds of several species of the genus *Cuphea*. *C. painteri*, for example, is rich in caprylic acid (73%), while *C. carthagenensis* oil consists of 81% lauric acid and *C. koehneana* oil capric acid (95%). These oils are highly saturated and are suitable for use in this application either individually (e.g. high lauric *C. carthagenensis*) or as oil blends of high lauric and high caprylic and/or capric *Cuphea* oils. If used in a blend, as noted above, total level of lauric acid in oil blend, for purposes of our invention, is at least 30%.

Lauric oils, suitable for use in this application, may be produced by genetic engineering techniques. Lauric algal oil from Solazyme® is one example.

In addition to defined oils, the oil phase may comprise oil soluble skin beneficial actives such as, for example, Vitamin A, Vitamin E, sunscreens, fragrances, retinol palmitate, esters of 12 hydroxystearic acid, conjugated linoleic acid; antibacterial agents; mosquito repellents; essential oils etc. at level of 0.01 to 5%.

Another ingredient which could be found in the oil phase is an oil phase stabilizer. For example, small amounts (0.01 to 2% preferably 0.1 to 1% by wt. nanoemulsion) of antioxidants may be used. A preferred antioxidant is butylated hydroxytoluene (BHT).

Finally, in one aspect of the invention, the invention provides that the oil phase comprises 0.1 to 7% by wt. nanoemulsion composition fatty acid having melting point of −10° C. to 30° C., preferably −5° C. to 25° C. or 0° C. to 20° C.; or mixture of fatty acids with melting point of the mixture of −10° C. to 30° C., preferably −5° C. to 25 or 0° C. to 20° C. This is a required component for the claims of the subject application relating to concentrate-dilution process. It should be noted that fatty acids discussed here are free fatty acids, not to be confused with the fatty acids ester-linked to glycerol moiety in triglyceride oils as discussed previously.

The fatty acids or fatty acid mixtures suitable for this application with melting points −10° C. to 30° C. are listed below.

Saturated branched fatty acids typically have a low melting point compared with their linear counterpart. Their solubility in organic solutions is high and so is the solubility of their corresponding salts in aqueous solutions. A typical example is isostearic acid (methyl heptadecanoic acids), which is a liquid isomer of stearic acid consisting of a mixture of monobranched fatty acids. Commercially available isostearic acids include, e.g., Emersol® 3875 with up to 80% isostearic and isopalmitic acid, produced by Emery Oleochemicals and Prisorine™ 3505 produced by Croda. The cosmetic-grade isostearic fatty acids are water white in color, the iodine value is about 3.0 or less, and the melting point is about 6° C.

Unsaturated fatty acids with a single double bond such as myristoleic acid has a melting point of about 4° C. and oleic acid has a melting point of 16° C. Unsaturated fatty acids with two or more double bonds with a melting of point of about 0° C. to 30° C., e.g. linoleic acid, are also suitable to this application.

Saturated straight chain fatty acids with a chain length less than 10 carbons, e.g. caprylic acid has a melting point of 17° C.

Fatty acid mixtures suitable to this application can be the mixture of fatty acids each with a melting point below 30° C. mixed in any ratio.

A fatty acid with melting point above 30° C. and one with melting point below 30° C. can be mixed with a specific ratio such that the melting point of the mixture is below 30° C. e.g. isostearic acid and lauric acid mixed in a ratio of 70/30 (wt. %).

Another way to obtain fatty acid mixtures with melting point lower than 30° C. is by mixing fatty acids that can form a binary eutectic mixture, whose melting temperature is lowest. For example, suitable for this application, capric acid-lauric binary system forms a eutectic with the mixture ratio of 66:34 (wt. %), which melts at 20° C., lower than 32° C. (capric acid's melting point) and 44° C. (lauric acid's melting point), both of which is out of the scope of this application. Another example, oleic acid can form eutectic mixtures with lauric and myristic acid respectively, with melting point of eutectic mixtures of about 10° C.

Also suitable for this application are coconut fatty acids or palm kernel fatty acids which are mixtures of $C_8$ to $C_{22}$ fatty acid with a melting point of 22-26° C.

Lauric acid alone, for example, has a melting point greater than 40° C. and fails to produce desirable transparent nanoemulsion. However, a 50:50 mixture (wt. %) of lauric and isostearic acid has melting point below 25° C. and produces the desired transparent nanoemulsions as defined by NTU values noted.

Aqueous Phase

The aqueous phase comprises water soluble surfactant system comprising water soluble surfactants which are selected from the group consisting of anionic surfactants, amphoteric surfactants and mixtures thereof, wherein the anionic surfactant comprises 15% or more, preferably 40% or more anionic. Although these may be 100% anionic, preferably there is at least some amphoteric surfactant present and anionic comprises 15% to 95% or 40 to 85% of the surfactant system.

One class of anionic surfactant which may be used are alkyl and alkyl ether sulfates, having respective formulae $ROSO_3M$ and $RO(C_2H_4O)_xSO_3M$, where R is alkyl or alkenyl of about 8 to 18 carbons. X is an integer of 1 to 10, and M is a cation such as ammonium; alkanolamine, such as triethanolamine; monovalent metal, such as sodium and potassium.

Other suitable anionic surfactants are the water-soluble salts of organic, sulfuric acid reaction products confirming to the formula $[R^1—SO_3\text{-}M]$ where $R^1$ is a straight or branched chain, saturated, aliphatic hydrocarbon radical having from about 8 to about 24, preferably from about 10 to about 18, carbon atoms; and M is a cation described hereinbefore.

Still other suitable anionic detersive surfactants are the reaction products of fatty acids esterified with isethionic acid and neutralized with potassium hydroxide where, for example, the fatty acids are derived from coconut oil or palm kernel oil; potassium salts of fatty acid amides of methyl taurate in which the fatty acids, for example, are derived from coconut oil or palm kernel oil.

Other anionic surfactants suitable for use in the compositions are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic surfactants include olefin sulfonates having from about 10 to about 24 carbon atoms. In addition to the true alkene sulfonates and a proportion of hydroxyl-alkanesulfonates, the olefin sulfonates can contain minor amounts of other materials, such as alkene disulfonates depending upon the reaction conditions, proportion of reactants, the nature of the staring olefins and impurities in the olefin stock and side reactions during the sulfonation process.

Another class of anionic surfactants suitable for use in the compositions is the beta-alkyloxy alkane sulfonates. These surfactants conform to the Formula (1):

where $R^1$ is a straight chain alkyl group having from 6 to about 20 carbon atoms, $R^2$ is a lower alkyl group having from 1 to 3 carbon atoms, preferably 1 carbon atom, and M is a water-soluble cation as described hereinbefore.

Preferred anionic surfactants for use in the compositions include ammonium lauryl sulfate, ammonium laureth sulfate, trimethylamine lauryl sulfate, trithylamine laureth sulfate, triethanolamine lauryl sulfate, triethanolamine laureth sulfate, monoethanolamine lauryl sulfate, monethanolamine lauryl sulfate, diethanolamine lauryl sulfate, diethanolamine lauryl sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, ammonium cocoyl sulfate, ammonium lauryl sulfate, sodium cocoyl sulfate, sodium lauroyl sulfate, potassium cocoyl sulfate, potassium lauryl sulfate, triethanolamine lauryl sulfate, triethanolamine lauryl sulfate, monethanolamine cocoyl sulfate, monoethanolamine lauryl sulfate, sodium tridecyl benzene sulfonate, sodium dodecyl benzene sulfonate and combinations thereof.

Another preferred class of anionics are salts of N-acyl derivatives of amino acids.

Preferred emulsifiers are acylglutamate, acylaspartate, acylglycinate and acylalaninate surfactants. Preferably, these are potassium and/or sodium salts of acylglutamate or acyl aspartate or acylglycinate or acylalaninate, wherein greater than 65% of the acyl chains has chain length $C_{14}$ or less, e.g., $C_8$ to $C_{14}$ (e.g., derived from coconut fatty acid). The acyl chains preferably have greater than 75%, more preferably greater than 80% $C_{14}$ or less chain length. Preferably, greater than 75%, most preferably greater than 80% of the chain length are $C_{12}$, $C_{14}$ or mixtures thereof.

There are two formats of amino acid surfactants commercially available. One is powder or flake format, which is typically more expensive and high in purity. Examples of solid dicarboxylic amino acid surfactants include:

sodium N-cocoyl-L-glutamate (e.g., Amisoft® CS-11 by Ajinomoto)
sodium N-lauroyl-L-glutamate (e.g., Amisoft® LS-11 by Ajinomoto)
sodium N-myristoyl-L-glutamate (Amisoft® MS-11 by Ajinomoto)
potassium N-cocoacyl_I-Glutamate (e.g., Amisoft® CK-11 by Ajinomoto)
potassium N-myristoyl-L-glutamate (Amisoft® MK-11 by Ajinomoto)
potassium N-lauroyl-L-glutamate (Amisoft® LK-11 by Ajinomoto)
sodium lauroyl aspartate (AminoFoamer™ FLMS-P1 by Asahi Kasei Chemical Corporation)
sodium lauroyl glutamate (Aminosurfact™ ALMS-P1/S1 by Asahi Kasei Chemical Corporation)
sodium myristoyl glutamate (Aminosurfact™ AMMS-P1/S1 by Asahi Kasei Chemical Corporation)

Examples of solid monocarboxylic amino acid surfactants include:

sodium cocoyl glycinate (e.g., Amilite® GCS-11 by Ajinomoto)
potassium cocoyl glycinate (e.g., Amisoft® GCK-11 by Ajinomoto)

Liquid amino acid surfactants typically contain 20 to 35% surfactant active, high in pH and inorganic salt (e.g. 3 to 6% NaCl). Examples include:

AMISOFT® ECS-22SB: Disodium Cocoyl Glutamate (30% Aqueous Solution)
AMISOFT® CS-22: Disodium Cocoyl Glutamate sodium Cocoyl Glutamate (25% Aqueous Solution)
AMISOFT® CK-22: Potassium Cocoyl Glutamate (30% Aqueous Solution)
AMISOFT® LT-12: TEA-Lauroyl Glutamate (30% Aqueous Solution)
AMISOFT® CT-12 TEA-Cocoyl Glutamate (30% Aqueous Solution)
AMILITE® ACT-12: TEA-Cocoyl Alaninate (30% Aqueous Solution)
AMILITE® ACS-12: Sodium Cocoyl Alaninate (30% Aqueous Solution)
AMILITE® GCK-12/GCK-12K: Potassium Cocoyl Glycinate (30% Aqueous Solution)
Aminosurfact™ ACDS-L: Sodium Cocoyl Glutamate (25% Aqueous Solution)

Aminosurfact™ ACDP-L: Potassium Cocoyl Glutamate (22%)+Sodium Cocoyl
Glutamate (7%)
Aminosurfact™ ACMT-L: TEA-Cocoyl Glutamate (30% Aqueous Solution)
AminoFoamer™ FLDS-L: Sodium Lauroyl Aspartate (25% Aqueous Solution)

Amphoteric surfactants preferably include derivatives of aliphatic secondary and tertiary amines, in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Preferred amphoteric surfactants for use in the present invention include cocoamphoacetate, cocoamphodiacetate, lauroamphoacetate, lauroamphodiacetate, and mixtures thereof. Preferred zwitterionic surfactants are derivatives of aliphatic quaternary ammonium, phosphonium, and sulfonium compounds, in which the aliphatic radicals can be straight or branched chain, and wherein one of the aliphatic substituents contains from 8 to 18 carbon atoms and one contains an anionic group such as carboxy, sulfonate, sulfate, phosphate or phosphonate. Zwitterionics such as betaines are preferred.

In addition, in the subject application the external aqueous phase comprises 55 to 90% by wt. nanoemulsion of water and glycerol wherein ratio of glycerol to water is at least 2.5:1, preferably 2.8:1 to 10:1, most preferably 3:1 to 5:1.

For compositions produced using the process of the invention (where only one pass through high pressure homogenizer is needed to obtain composition of less than 45 NTU), the final diluted composition also has 55 to 90% water and glycerol but, as noted previously, the initial ratio of glycerol to water (in intermediate concentrate emulsion) is 1:2 to 2:1.

In compositions (which are produced by non-concentrate-dilution process) comprising the anionic surfactant and the lauric oils of our invention, applicants have discovered that a minimum floor ratio of glycerol to water is critical to ensure transparency. If the ratio of glycerol is too low (e.g., below 2.5:1 glycerol to water), the transparency disappears.

Due to high level of glycerol, the level of water activity is within the ranges to inhibit bacteria growth, and potentially allows use of only fungicide or even no preservatives in nanoemulsions as a final product.

Another factor in maintaining transparency has been found to be processing the compositions with at least 1 pass, preferably 2 passes (or more if desired) through a high pressure homogenizer. The homogenization pressure is preferably 7000 pounds per square inch (psi) or less (482.6 bar or less), preferably 6000 psi or less (413.6 bar or less), preferably 1500-5000 psi (103.4 to 344.7 bar).

In another aspect, the subject matter of the subject application, the invention relates to an energy efficient concentrate-dilution process involving only one pass through the high pressure homogenizer. This process relates to concentrate emulsions comprising additional fatty acid in the oil phase and a lower ratio of glycerol to water in the aqueous phase (1:2 to 2:1). As described below, the process relates to forming a concentrate emulsion with high amounts of oil (greater than 45% to 80% by wt. composition) and a lower ratio of glycerol to water in the aqueous phase (1:2 to 2:1), intensively mixed by a conventional rotor/stator high shear device at a rotor speed of 3000 to about 7000 rpm, diluting to a desired oil concentration (5 to 40% by wt. of composition) and to a desired glycerol-to-water ratio (at least 2.5:1, preferably 2.8:1 to 10:1, most preferably 3:1 to 5), and subsequently subjecting the final composition to only one pass homogenization (i.e., through high pressure homogenizer) while still obtaining better transparency values than that obtained with one pass through the high pressure homogenizer in non-concentrate-dilution process.

The compositions prepared generally according to the composition and processes of our co-pending invention have a transparency value of 100 NTU or less, preferably 90 NTU or less, more preferably 60 or less. According to the specific concentrate-dilution process of the present application, NTU values are at low end (e.g., less than 45, preferably 35 or less), but using only one pass. Such low values are also achieved using non-concentrate-dilution processes which is used, for example, in co-pending application, but at least two passes through a high pressure homogenizer are required. This is much more energy intensive.

Preparation of Nanoemulsion

Non-Concentrate-Dilution Process (Used in Co-Pending Application)

Nanoemulsions are typically formed in a two stage process.

The first mixing stage is used to form a coarse emulsion. The oil phase and aqueous phase were heated to from ambient temperature to 60° C. separately such that each phase was clear and uniform; then the oil phase was mixed with the aqueous phase with intensive mixing in a conventional mixer. Intensive mixing can be accomplished via conventional means including mixing the materials in a stirred tank and passing the mixture through a rotor/stator mixer such as the Silverson® high shear in-line mixer or mixing them in the vessel with a high shear mixer such as the Scott® Turbon mixer. Alternatively, the coarse emulsion may be created by using a continuous high shear mixing device such as the standard sonolator device produced by Sonic Corporation of Connecticut. These standard sonolators are normally operated at pressures of 200-500 psi (13.8 to 34.5 bar) to form coarse emulsion.

The second stage of the process is to pass the coarse emulsion through a high pressure homogenizer to form the nanoemulsion. Suitable high pressure homogenizers are the Nano DeBee homogenizer of BEE International (Massachusetts, USA) and the high pressure sonolator device also produced by Sonic Corporation of Connecticut, USA. These devices can be operated up to 1500-5000 psi (103.4 to 344.7 bar) in order to produce nanoemulsions of less than 100 nm. For lauric oils, for example either coconut oil or palm kernel oil, only one or two passes through the Nano DeBEE or high pressure sonolator is required to reach the desired nanoemulsion particle size and transparency, with or without fatty acid present in the oil phase.

Concentrate-Dilution Process of Subject Application

In the subject matter of the subject application, a concentrate emulsion comprising fatty acid or mixture of fatty acid having melting point of 30° C. or lower is first prepared. Oil(s) in oil phase are present as greater than 45% by wt, preferably 50 to 85% of nanoemulsion. The concentrate is also prepared with aqueous phase comprising glycerol and water, where ratio of glycerol to water is 1:2 to 2:1. The concentrate is intensively mixed by a conventional rotor/stator high shear device at a rotor speed of 3000 to about 7000 rpm (which differs from energy intensive, high-pressure homogenizer); the concentrate is then diluted by mixing a solution of water, glycerol or additional surfactant in a separate container and combining with the concentrated nanoemulsion to obtain the final emulsion wherein oil is present at level of 40% or below, preferably 5 to 40% and the ratio of glycerol to water is at least 2.5:1, preferably 2.8:1 to 10:1, most preferably 3:1 to 5:1. Preferably, the 5 to 40% oil is lauric oil(s). As noted up to 30% (0 to 30%) of the 5 to 40% oil(s) may be non-lauric such that oil (after dilution)

may comprise 3.5% (30% of 5% or 1.5% may be non-lauric) to 40% (assuming 100% lauric oil at start) lauric oil. Finally, the diluted mixture is passed through a high pressure homogenizer at 6000 psi or less (413.6 bar or less), preferably 1500 to about 5000 psi (103.4 to 344.7 bar) for one pass. Surprisingly, these nanoemulsion have a far lower NTU and higher viscosity than nanoemulsions containing fatty acids prepared without going through concentrate-dilution process.

In the examples, the following terms are defined as noted below:

Pass#: the number of times the emulsion passes through high pressure homogenizer D[4,3]: Volume average diameter or mean diameter or volume average size determined by a Malvern Mastersizer.

Turbidity: Measured by a turbidity meter HACH 2100N at ambient temperature.

Viscosity: measured by Discovery Hybrid Rheometer at 25° C. and at 4 s$^{-1}$

EXAMPLES

Examples 1-11 and comparatives A-G are to illustrate the non-concentrate-dilution process, while Examples 12-13 are to demonstrate the more energy efficient concentrate-dilution process.

Examples 1-4 and Comparatives A-B

Coarse emulsions were prepared in a one liter ESCO mixer equipped with a rotor/stator high shear device (ESCO-LABOR AG, Switzerland). The aqueous phase was added to the ESCO mixer and heated up to 40° C. or until clear. The oil phase was combined and heated up to 40° C. or till molten in a separate container. The oil phase was gradually added to the aqueous phase in the ESCO mixer under agitation and/or was intensively mixed by the rotor/stator device. When the addition of all oil phase was completed and the coarse emulsion was formed in the ESCO mixer, the coarse emulsion was transferred and passed through a high pressure homogenizer Nano DeBEE 2 times to arrive at the desired turbidity at a process pressure of 5000 psi (344.7 bar).

| Ingredient | Comp. A | Ex 1 | Ex 2 | Ex 3 | Ex 4 | Comp B |
|---|---|---|---|---|---|---|
| | | | Wt. % | | | |
| Oil Phase | | | | | | |
| Isopropyl palmitate | | | | | | 10 |
| Carnation ® White Mineral oil | | | | | | 25 |
| Coconut oil | | 35 | 10 | 35 | 10 | |
| High Oleic sunflower oil | 35 | | | | | |
| BHT | | | 0.1 | | | |
| Fragrance | 1.1 | 1.1 | 1.1 | | | |
| Aqueous phase | | | | | | |
| Glycerol | 47 | 47 | 65.4 | 47.2 | 65.4 | 45.5 |
| water | Q.S**. | Q.S**. | Q.S**. | Q.S** | Q.S**. | Q.S**. |
| Sodium lauryl ether sulfate SLES.1EO (70%) | 6.5 (4.5)* | 6.5 (4.5)* | 9.0 (6.3)* | | | |
| Cocoamidopropyl betaine (28%) | 5.4 (1.5)* | 5.4 (1.5)* | 7.5 (2.1)* | 5.2 (1.5)* | 7.5 (2.1)* | 5.2 (1.5)* |
| Potassium Cocoyl Glutamate | | | | 4.55 | 6.31 | 4.39 |
| KOH | | | | 0.4 | 0.5 | 0.5 |
| Number of passes At 5000 psi | | | 2 | | | |
| D$_{[4,3]}$ nm | 62 | — | — | 65 | — | — |
| pH | 5.3 | 5.7 | 5.6 | 6.3 | 6.21 | 7.23 |
| Turbidity, NTU | 163 | 32.8 | 22.5 | 17.5 | 19.7 | 199 |

*number in parenthetical is present as active
**quantum sufficit (as much as is sufficient)

The surfactant systems in Examples 1-4 and Comparatives A-B consist of anionic surfactant (potassium cocoyl glutamate or sodium lauryl ether sulfate) and amphoteric surfactant (cocoamidopropyl betaine) at a ratio of 3 to 1. Comparatives A and B relative to Examples 1-4 demonstrate that excellent transparency (measured by a turbidity meter HACH 2100N) of less than 40 NTU was achieved by lauric oil, specifically coconut oil, but not by other non-lauric oils.

Examples 5-8 and Comparatives C-E

Examples 5-8 and Comparatives C-E were prepared similarly to Examples 1-4 and Comparatives A-B.

| Ingredient | Comp C | Ex 5 | Ex 6 | Comp D Wt. % | Comp E | Ex 7 | Ex 8 |
|---|---|---|---|---|---|---|---|
| Oil Phase | | | | | | | |
| Ultimate ®76 Coconut oil | | | | 35 | | | |
| BHT | | | | 0.1 | | | |
| Lauric acid | | | | | 0.9 | 0.9 | 0.9 |
| Prisorine ™ 3505 Isostearic Acid | | | | | 2.0 | 2.0 | 2.0 |
| Fragrance | | | | 2.2 | | | |
| Aqueous phase | | | | | | | |
| Glycerol | 44.6 | 44.6 | 44.6 | 32 | 42.6 | 42.6 | 42.6 |
| Water | Q.S | Q.S | Q.S. | Q.S. | Q.S. | Q.S. | Q.S. |
| Eversoft ULS-30S (Sodium lauroyl glutamate 25%) | | 10.5(2.6)* | | | 10.1(2.5) | | |
| Cocoamidopropyl betaine (38%) | | 6.9(2.6) | | | 6.6(2.5) | | |
| Sodium Hydroxide | | | | | 0.11 | | |
| Number of passes At 5000 psi | 0 | 1 | 2 | 2 | 0 | 1 | 2 |
| $D_{[4.3]}$ nm | 1468 | 93 | — | 70 | 556 | 77 | 75 |
| pH | 7.37 | 7.37 | 7.17 | 7.78 | 6.93 | 6.88 | — |
| Turbidity, NTU | 378 | 50.4 | 13.2 | 939 | 2352 | 88 | 17.8 |
| Viscosity (at 4 $s^{-1}$, 25 C.), Pa · s | — | 0.98 | 3.00 | 0.16 | 2.77 | 1.12 | 18.99 |

*Number in parenthetical is percent as active ingredient.

The surfactant systems in Examples 5-8 and comparatives C-E comprise anionic surfactant (sodium lauroyl glutamate) and amphoteric surfactant (cocoamidopropyl betaine) at a ratio of 1 to 1.

Comparative C relative to Examples 5 and 6 demonstrates that, to achieve optimum turbidity below 100 NTU, preferably below 60, the composition should be passed through homogenizer at pressure of 5000 psi or less for at least 1 pass (Example 5), preferably 2 passes (Example 6). In Comparative D, water is present at about 25.5% by wt. (100−(35+0.1+2.2+32+2.6+2.6)), and ratio of glycerol to water is about 1.25 to 1. By contrast, in Examples 5 and 6, water is about 12.9% (100−(35+0.1+2.2+44.6+2.6+2.6)) and ratio of glycerol to water is well above 2.5:1 (about 3.46:1 in examples). It is seen that glycerol/water ratio is a further criticality.

In Examples 7, 8 and Comparative E, 0.9% lauric acids is added to the composition as well as 2.0% isostearic acid. The fatty acid mixture (lauric/isostearic=3/7) has a melting point below 20° C. Adding fatty acids does not provide any advantages while yielding worse transparency measured by Turbidity value if comparing comparatives C vs. E and Examples 5 vs. 7. Surprisingly, after two passes through the homogenizer, the transparent nanoemulsion with fatty acids present in Example 8 results in a viscosity 6 times as large as that of Example 6 (without fatty acids present). Transparent gel like consistency is another attribute desired by consumers.

Examples 9-11 and Comparatives F-G

Examples 9-10 and Comparatives F-G were prepared similarly to Examples 1-4 and Comparatives A-B.

| Ingredient | Comp F | Comp G | Example 9 | Example 10 | Example 11 |
|---|---|---|---|---|---|
| Oil Phase | | | Wt. % | | |
| Ultimate ®76 Coconut oil | | | 35 | | |
| Hydrogenated Palm Kernel Oil | | | | | 35 |
| Lauric acid | 2.9 | 2.9 | 1.45 | 0 | 0 |
| Prisorine ™ 3505 Isostearic Acid | 0 | 0 | 1.45 | 2.9 | 2.9 |
| BHT | | | 0.1 | | |
| Aqueous phase | | | | | |
| Glycerol | | | 43.5 | | |
| Water | | | q.s | | |
| Galsoft KCGL (Potassium Cocoyl Glutamate, 30%) | | | 14.0(4.2) | | |
| TEGO BETAIN C 60 (Cocoamidopropyl Betaine, 47%) | | | 3.0(1.4) | | |
| Number of passes At 5000 psi | 1 | 2 | 1 | 1 | 1 |
| pH | 6.95 | 7.11 | 7.16 | 7.37 | 7.17 |
| Turbidity (at 25 C.), NTU | Solidified Not transparent (When at 40 C., fluid and transparent) | 55.2 | 49.6 | 65.2 | |

* Number in parenthetical is percent as active ingredient.

The surfactant systems in Examples 9-11 and Comparatives F-G consist of anionic surfactant (sodium lauroyl glutamate) and amphoteric surfactant (cocoamidopropyl betaine) at a ratio of 3 to 1.

Fatty acid, such as lauric acid, having melting point greater than 40° C. (see Comparative Examples F & G), resulted in non-transparent nanoemulsions at ambient temperature. Fatty acid, e.g. isostearic acid and fatty acid mixture (lauric/isostearic) having melting point below 25° C. (Examples 9 and 10), resulted in transparent nanoemulsions at ambient temperature.

Surprisingly, hydrogenated palm kernel oil, having a melting point about 40° C. (Example 11), yielded a transparent fluid composition. This is surprising because, even when oil has melting point this high, fluid transparent nanoemulsion was still formed.

Example 12

The composition as shown in Example 12c of a transparent nanoemulsion is the same as that of Example 7, but was prepared with the method of concentrated emulsion-dilution.

Step 1: Preparation of Concentrated Emulsion:

Emulsions were prepared in a one liter ESCO mixer equipped with a rotor/stator high shear device (ESCO-LABOR AG, Switzerland). The aqueous phase, including liquid surfactant, glycerol, and water were added to the ESCO mixer; mixed to uniformity; and heated up to about 30 to about 40° C. The oil phase was combined and heated up to about 40° C. or until melted in a separate container, was gradually added to the aqueous phase in the ESCO mixer under agitation with a scraper. When the addition of all oil phase was completed, the mixture in the ESCO mixer was intensively mixed by the rotor/stator device at 3000 RPM to 7000 RPM (rotor speed) for up to 5 minutes. The oil droplet size was measured by a Malvern Mastersizer.

| Ingredient | Example 12a Wt. % |
|---|---|
| Oil Phase | |
| Ultimate ®76 Coconut oil | 56 |
| BHT | 0.2 |
| Lauric acid | 1.4 |
| Prisorine ™ 3505 Isostearic Acid | 3.3 |
| Fragrance | 3.5 |
| Aqueous phase | |
| Glycerol | 15.6 |
| Water | Q.S. |
| Eversoft ULS-30S (sodium lauroyl glutamate, 25%) | 11.0(2.8)* |
| Cocoamidopropyl betaine (38%) | 9.0(3.4)* |
| $D_{[4,3]}$, nm | 144 |

*Number in parenthetical is percent as active ingredient.

In this step, the oil phase consists of 56% coconut oil, far more than 35% coconut oil in Example 7. Fatty acids and Fragrance are proportionately more as well. In the aqueous phase, the glycerol/water ratio is about 1.1.

Step 2. The Concentrated Emulsion was Diluted for Further Processing

The diluent as shown in Example 12b was premade by mixing all ingredients in a separate container with overhead stirrer, then was combined in a one liter ESCO with the concentrated emulsion shown in Example 12a at a ratio of 37.5/62.5, arriving a composition as shown in Example 12c, which is the same composition as that of example 7, with an oil level of 35%. The mixture was mixed to uniform with the scraper at 40 to about 70 revolution per minute (RPM) while maintaining a temperature of 30 to 40° C.

| Ingredient | Example 12b Wt. % |
|---|---|
| Glycerol | 87.4 |
| Water | Q.S |
| Eversoft ULS-30S (sodium lauroyl glutamate 25%) | 8.4(2.1)* |
| Cocoamidopropyl betaine (38%) | 2.6(1.0)* |
| NaOH | 0.3 |

*Number in parenthetical is percent as active ingredient.

Step 3. Homogenization

The diluted emulsion as shown in Ex 12c was passed through a High Pressure homogenizer Nano DeBEE at 5000 psi (344.7 bar) once, yielding a nanoemulsion with a turbidity of 24.3 NTU vs. 88 NTU in Ex 7 and viscosity of 2.1 Pa·s vs 1.1 in Ex 7.

| Ingredient | Ex 12c Wt. % |
|---|---|
| Oil Phase | |
| Ultimate ®76 Coconut oil | 35 |
| BHT | 0.1 |
| Lauric acid | 0.9 |
| Prisorine ™ 3505 Isostearic Acid | 2.0 |
| Fragrance | 2.2 |
| Aqueous phase | |
| Glycerol | 42.6 |
| Water | Q.S. |
| Eversoft ULS-30S (sodium lauroyl glutamate 25%) | 10.1(2.5)* |
| Cocoamidopropyl betaine (38%) | 6.6(2.5)* |
| Sodium Hydroxide | 0.11 |
| Number of passes At 5000 psi | 1 |
| $D_{[4,3]}$ nm | 69 |
| pH | 6.7 |
| Turbidity, NTU | 24.3 |
| Viscosity (at 4 $s^{-1}$, 25° C.), Pa · s | 2.1 |

*Number in parenthetical is percent as active ingredient.

Example 13

Example 13 was prepared similarly to Example 12, except that palm kernel oil was used.

Step 1. Preparation of Concentrated Emulsion

Example 13a was prepared similarly to Example 12, except that palm kernel oil was used.

| Ingredient | Ex 13a Wt. % |
|---|---|
| Oil Phase | |
| Palm Kernel Oil | 56 |
| BHT | 0.2 |
| Lauric acid | 1.4 |
| Prisorine ™ 3505 Isostearic Acid | 3.3 |
| Fragrance | 3.5 |
| Aqueous phase | |
| Glycerol | 15.6 |
| Water | Q.S. |
| Eversoft ULS-30S (sodium lauroyl glutamate, 25%) | 11.0(2.8)* |

-continued

| Ingredient | Ex 13a Wt. % |
|---|---|
| Cocoamidopropyl betaine (38%) | 9.0(3.4)* |
| $D_{[4,3]}$ nm | 158 |

*Number in parenthetical is percent as active ingredient.

Step 2. The Concentrated Emulsion was Diluted for Further Processing.

Diluent shown in Example 13b was combined in a one liter ESCO with the concentrated emulsion shown in Example 13a at a ratio of 37.5/62.5, arriving a composition as shown in Ex13c.

| Ingredient | Example 13b Wt. % |
|---|---|
| Glycerol | 87.4 |
| Water | Q.S |
| Eversoft ULS-30S (Sodium lauroyl glutamate 25%) | 8.4(2.1)* |
| Cocoamidopropyl betaine (38%) | 2.6(1.0)* |
| NaOH | 0.3 |

*Number in parenthetical is percent as active ingredient.

Step 3. Homogenization

The diluted emulsion as shown in Example 13c was passed through a high pressure homogenizer Nano DeBEE at 5000 psi (344.7 bar) once, yielding a nanoemulsion with a turbidity of 31 NTU and viscosity of 2.1 Pa·s, similar to that of Example 12c.

| Ingredient | Example 13c Wt. % |
|---|---|
| Oil Phase | |
| Ultimate ®76 Coconut oil | 35 |
| BHT | 0.1 |
| Lauric acid | 0.9 |
| Prisorine ™ 3505 Isostearic Acid | 2.0 |
| Fragrance | 2.2 |
| Aqueous phase | |
| Glycerol | 42.6 |
| Water | Q.S. |
| Eversoft ULS-30S (Sodium lauroyl glutamate 25%) | 10.1(2.5)* |
| Cocoamidopropyl betaine (38%) | 6.6(2.5)* |
| Sodium Hydroxide | 0.11 |
| Number of passes At 5000 psi | 1 |
| $D_{[4,3]}$ nm | 71 |
| pH | 6.7 |
| Turbidity, NTU | 31 |
| Viscosity (at 4 s$^{-1}$, 25° C.), Pa·s | 2.1 |

*Number in parenthetical is percent as active ingredient.

The invention claimed is:

1. A process for making an oil-in-water nanoemulsion comprising:
   1) an internal oil phase comprising (a) 3.5 to 40% by wt. nanoemulsion composition of a lauric oil; wherein there is a minimum 5% total of lauric and non-lauric triglyceride oil, and wherein said lauric oil is an oil or oils where saturated $C_{12}$ length fatty acid (12:0) comprises 30% to 85% of the fatty acid composition of the oil or oils and (b) 0.1 to 7% by wt. nanaemulsion of a fatty acid or mixture of fatty acids, wherein the fatty acid or mixture has melting temperature of −10° C. to 30° C.; and
   2) an external aqueous phase comprising:
      i. 55 to 90% by wt. nanoemulsion of water and glycerol, wherein the ratio of said glycerol to said water is 2.5:1 and higher; and
      ii. 3 to 12% of a surfactant system comprising water soluble surfactants selected from the group consisting of anionic surfactants, amphoteric surfactants and mixtures thereof, wherein said anionic surfactant comprises 15% or more, of the total surfactant system;
   wherein said composition has a turbidity of less than 45 NTU,
   wherein said nanoemulsion is prepared by:
      a) first preparing an intermediate concentrate emulsion containing:
         i. an oil phase additionally comprising fatty acid or mixture of fatty acids having melting point −10° C. to 30° C.; where said oil phase comprises 50 to 85% of the said concentrate emulsion and fatty acid or mixture comprises 1 to 15% of the said concentrate emulsion; and
         ii. an aqueous phase comprising a surfactant system, glycerol and water wherein the ratio of said glycerol to said water is 1:2 to 2:1, and said aqueous phase comprises 15 to 50% of the said concentrate emulsion;
         iii. heating aqueous and oil phase to a temperature ranging from ambient to 60° C. separately; and
      a) mixing said aqueous phase and said oil phase by conventional rotor/stator high shear device at rotor speed of 3000 to 7000 rpm to form concentrate emulsion or
      b) alternatively pumping both aqueous and oil phase simultaneously through a low pressure homogenizer at pressure of 13.8 to 34.5 bar (200 to 500 psi) to form concentrate emulsion; wherein oil droplets formed in said concentrated emulsion have an average particle size, D[4,3], of 100 to 350 nm;
      b) diluting the concentrate emulsion to oil range of 3.5 to 40% by wt. emulsion and to the ratio of glycerol to water ranging from 2.8:1 to 10:1; and
      c) passing through high pressure homogenizer at pressure of 413.6 bar (6000 psi) or less,
   wherein the pass through high pressure homogenizer of step (c) is done only once and results in said final oil-in-water nanoemulsion having, subsequent to preparation of concentrate emulsion and dilution, a turbidity of less than 45 MTU.

2. The process according to claim 1, wherein oil droplets formed in final nanoemulsion after dilution and homogenization have an average D[4,3] particle size of 100 nm or lower.

3. The process according to claim 2, wherein the average D[4,3] particle size is 20 to 95.

4. The process according to claim 1, wherein the anionic surfactant in the nanoemulsion is selected from the group consisting of alkyl sulfates, alkyl ether sulfates, N-acyl derivatives of amino acid and mixtures thereof.

5. The process according to claim 1, wherein said lauric oil used in the nanoemulsion is selected from the group consisting of coconut oil, palm kernel oil, babassu oil, tukum oil, murumuru oil, ouricuri oil, cohune oil, cuphea oil, lauric algal oil and mixtures thereof.

6. The process according to claim 1, wherein lauric oils comprise 30% to 85% lauric acid ester linked to glycerol moiety.

7. The process according to claim 6, wherein lauric oils comprise 40% to 55% lauric acid ester linked to glycerol moiety.

8. The process according to claim 1, wherein non-lauric triglyceride oils high in unsaturation with iodine value of above 50 partially replaces lauric oil at a level of 0 to 30% of lauric oil.

9. The process according to claim 8, wherein said non-lauric high IV oils are selected from the group consisting of sunflower oil, grapeseed oil, argan oil and mixtures thereof.

10. The process according to claim 8, wherein there is a minimum level of 3.5% lauric oil.

11. The process according to claim 1, wherein the melting temperature of the fatty acid is 0° C. to 25° C.

12. The process according to claim 1, wherein the ratio of said glycerol to said water in step 2 is 2.8:1 to 10:1.

13. The process according to claim 12, wherein the ratio of said glycerol to said water is 3.0:1 to 5:1.

14. The process according to claim 1, wherein said anionic surfactant comprises 40% or more of the total surfactant system.

15. The process according to claim 14, wherein said anionic surfactant comprises 40% to 85% of the total surfactant system.

16. The process according to claim 1, wherein said composition has a turbidity of less than 40 NTU.

17. The process according to claim 16, wherein said composition has a turbidity of 35 to 1.

18. The process according to claim 1, wherein the said pressure is 103. 4 to 344.7 bar (1500 to 5000 psi).

* * * * *